US009289267B2

(12) United States Patent
Sauer et al.

(10) Patent No.: US 9,289,267 B2
(45) Date of Patent: Mar. 22, 2016

(54) METHOD AND APPARATUS FOR MINIMALLY INVASIVE SURGERY USING ENDOSCOPES

(75) Inventors: Frank Sauer, Princeton, NJ (US); Ali Khamene, Princeton, NJ (US); Sebastian Vogt, Lawrenceville, NJ (US)

(73) Assignee: SIEMENS MEDICAL SOLUTIONS USA, INC., Iselin, NJ (US)

( * ) Notice: Subject to any disclaimer, the term of this patent is extended or adjusted under 35 U.S.C. 154(b) by 2365 days.

(21) Appl. No.: 11/383,598

(22) Filed: May 16, 2006

(65) Prior Publication Data

US 2006/0281971 A1 Dec. 14, 2006

Related U.S. Application Data

(60) Provisional application No. 60/690,339, filed on Jun. 14, 2005.

(51) Int. Cl.
*A61B 1/00* (2006.01)
*A61B 1/04* (2006.01)
*A62B 1/04* (2006.01)
*A61B 19/00* (2006.01)
*G06F 19/00* (2011.01)

(52) U.S. Cl.
CPC ............... *A61B 19/52* (2013.01); *A61B 1/0005* (2013.01); *A61B 1/04* (2013.01); *A61B 2019/5289* (2013.01); *G06F 19/3437* (2013.01)

(58) Field of Classification Search
USPC ......... 600/101, 103, 109, 111, 117, 118, 166, 600/407, 410, 415–417, 424–425, 429; 348/65
See application file for complete search history.

(56) References Cited

U.S. PATENT DOCUMENTS

| | | | |
|---|---|---|---|
| 5,825,908 A * | 10/1998 | Pieper et al. | 382/131 |
| 5,829,444 A | 11/1998 | Ferre et al. | |
| 5,868,675 A | 2/1999 | Henrion et al. | |
| 5,871,445 A | 2/1999 | Bucholz | |
| 5,891,034 A | 4/1999 | Bucholz | |
| 5,920,395 A | 7/1999 | Schulz | |
| 5,967,980 A | 10/1999 | Ferre et al. | |
| 5,971,997 A | 10/1999 | Guthrie et al. | |
| 6,016,439 A * | 1/2000 | Acker | 600/411 |
| 6,071,288 A | 6/2000 | Carol et al. | |
| 6,076,008 A | 6/2000 | Bucholz | |
| 6,122,541 A | 9/2000 | Cosman et al. | |
| 6,165,181 A | 12/2000 | Heilbrun et al. | |
| 6,346,940 B1 * | 2/2002 | Fukunaga | 345/427 |

(Continued)

*Primary Examiner* — Anhtuan T Nguyen
*Assistant Examiner* — Rynae Boler (57) ABSTRACT

A method and apparatus for presenting three-dimensional data to a physician is provided to facilitate the flexible navigation of an endoscope and surgical instruments with respect to anatomical structures. In accordance with a first embodiment a first set of data corresponding to a three dimensional model of a patient's anatomy is received. This three-dimensional model may be rendered from images taken in CT or MRI scanning, as discussed above. In accordance with this embodiment, this model is then combined with a second set of data corresponding to a view obtained from an endoscope. In another embodiment, the view from the illustrative endoscope is displayed as an inset image on the display of the three-dimensional image. In yet another embodiment, the three-dimensional image comprises a graphical representation of at least a first surgical instrument, such as said endoscope. The surgeon may select among various combinations of views and may zoom in or out from any particular view.

41 Claims, 5 Drawing Sheets

(56) References Cited

U.S. PATENT DOCUMENTS

| | | | |
|---|---|---|---|
| 6,445,943 B1 | 9/2002 | Ferre et al. | |
| 6,456,868 B2 * | 9/2002 | Saito et al. | 600/429 |
| 6,466,815 B1 * | 10/2002 | Saito et al. | 600/429 |
| 6,702,736 B2 * | 3/2004 | Chen et al. | 600/117 |
| 6,801,643 B2 * | 10/2004 | Pieper | 382/128 |
| 6,934,575 B2 | 8/2005 | Ferre et al. | |
| 6,980,849 B2 | 12/2005 | Sasso | |
| 6,980,921 B2 | 12/2005 | Anderson et al. | |
| 6,993,374 B2 | 1/2006 | Sasso | |
| 7,010,338 B2 | 3/2006 | Ritter et al. | |
| 7,020,512 B2 | 3/2006 | Ritter et al. | |
| 7,107,090 B2 * | 9/2006 | Salisbury et al. | 600/427 |
| 7,144,367 B2 * | 12/2006 | Chen et al. | 600/117 |
| 7,149,333 B2 * | 12/2006 | Pieper et al. | 382/128 |
| 7,162,292 B2 * | 1/2007 | Ohno et al. | 600/407 |
| 7,197,170 B2 * | 3/2007 | Dwyer et al. | 382/128 |
| 7,623,900 B2 * | 11/2009 | Graham et al. | 600/407 |
| 7,633,501 B2 * | 12/2009 | Wood et al. | 345/419 |
| 7,639,847 B2 * | 12/2009 | Middleton et al. | 382/128 |
| 7,640,050 B2 * | 12/2009 | Glenn et al. | 600/407 |
| 7,641,609 B2 * | 1/2010 | Ohnishi et al. | 600/117 |
| 7,653,426 B2 * | 1/2010 | Yatsuo et al. | 600/423 |
| 7,659,912 B2 * | 2/2010 | Akimoto et al. | 345/619 |
| 2001/0027272 A1 * | 10/2001 | Saito et al. | 600/426 |
| 2003/0018235 A1 * | 1/2003 | Chen et al. | 600/109 |
| 2003/0220541 A1 * | 11/2003 | Salisbury et al. | 600/101 |
| 2004/0193006 A1 * | 9/2004 | Chen et al. | 600/101 |
| 2005/0020876 A1 * | 1/2005 | Shioda et al. | 600/101 |
| 2005/0020878 A1 * | 1/2005 | Ohnishi et al. | 600/117 |
| 2005/0027193 A1 * | 2/2005 | Mitschke et al. | 600/427 |
| 2005/0182295 A1 * | 8/2005 | Soper et al. | 600/117 |
| 2005/0261550 A1 * | 11/2005 | Akimoto et al. | 600/117 |
| 2006/0149134 A1 * | 7/2006 | Soper et al. | 600/182 |
| 2006/0189842 A1 * | 8/2006 | Hoeg et al. | 600/118 |

* cited by examiner

METHOD AND APPARATUS FOR MINIMALLY INVASIVE SURGERY USING ENDOSCOPES

This patent application claims the benefit of U.S. Provisional Application No. 60/690,339, filed Jun. 14, 2005, which is hereby incorporated by reference herein in its entirety.

BACKGROUND OF THE INVENTION

The present invention relates generally to image guidance for minimally invasive surgery and, more particularly, to augmented reality visualization using endoscopes.

Minimally invasive surgery is becoming increasingly widespread due to the benefits to both the patient (i.e., decreased morbidity and faster recovery) as well as the benefits to the insurance industry (i.e., less hospitalization time and lower cost). Typically, minimally invasive surgery involves creating one or more small incisions and performing any surgical tasks through those incisions using specialized, frequently elongated, surgical tools.

As one skilled in the art will recognize, visual feedback is essential to such minimally invasive surgery. Typically, visual feedback in such surgery is obtained via an endoscope, which is an optical or optoelectronic viewing instrument that is inserted into a patient's body to provide a local view of the surgical site. As one skilled in the art will recognize, an endoscope is a small, flexible or rigid tube capable of imaging an area inside a patient's body via a lens connected to or integrated with the end of the tube. Light is delivered to the area to be imaged, for example, via one or more optical fibers within the tube. This light is reflected off of surfaces within the body and is focused by the lens onto the one or more optical fibers and delivered to a display in, for example, an operating room. Many different types of endoscopes have been developed for use in different surgical procedures. For example, flexible endoscopes are used for surgeries in the ear-nose-throat and gastrointestinal fields. Specialized flexible endoscopes, called bronchoscopes, are used for procedures in the bronchial tree of lungs. Rigid endoscopes are used in other types of procedures. For example, rigid endoscopes called laparoscopes and thoracoscopes are used in surgeries of the abdomen and thorax, respectively. The resulting images from such endoscopes are used by a surgeon to, for example, accurately position surgical instruments or to diagnose various conditions. The accuracy of position of the endoscope as well as the surgical instruments becomes increasingly important as the difficulty and delicacy of a procedure increases.

For example, positioning and visualization of an endoscope and surgical instruments is critical in surgical procedures such as minimally-invasive thoracoscopic spine surgery. The goal of such surgery is typically to remove a damaged disc between vertebrae or to fuse vertebrae by filling a gap between vertebrae with bony material which, over time, grows together with the vertebrae. Performing such spinal surgery without opening a patient's chest and, instead, using minimally invasive surgical techniques, poses several challenges. First, guiding instruments such as a thoracoscope to a specific vertebrae is difficult since a physician cannot simply count vertebrae along the spine from inside the thorax. Second, the thoracoscope's field of view is somewhat limited and, therefore, it is difficult to judge depth of penetration from only the endoscope's image. Success of the procedure, however, is highly reliant upon accurate three-dimensional positioning of the endoscope and manipulation of the surgical instruments in order to prevent potential damage to the spinal cord.

Recently, in some attempts to increase the information available to surgeons, visual information from an endoscope has been combined with virtual information, for example derived from a Computed Tomography (CT) or Magnetic Resonance Imaging (MRI) image collected prior to an operation. For example, in one such attempt, optical images from an endoscope were shown side by side on a display in the operating room with matching virtual images derived from such CT/MRI images. Thus, illustratively, a physician could see both a virtual and optical image of an area inside a patient's body and then, for example, the physician could manipulate the virtual display to "view" behind a structure or obstruction in the body. However, while this method provides added benefit over the use of an endoscope alone, it does not significantly add to the ability of navigating an endoscope in more difficult and delicate procedures.

In another attempt, virtual images of a patient's internal anatomy obtained via CT/MRI scanning are mapped to an actual image of the patient. Views produced by such a procedure are referred to herein and are known in the art as augmented reality views. In creating such an augmented reality view, the virtual images are registered to a patient coordinate system, represented by markers attached to the patient. A pointer, the position of which is tracked in reference to the patient coordinate system, can then be visualized in the context of the imaging system so that a user can look at a display and see a model of the pointer in relationship to the anatomical structures of the medical image. However, this method only uses the virtual images and the location of a pointer with no endoscopic or other local images. Therefore, such a method is not sufficient for the aforementioned delicate or difficult procedures.

SUMMARY OF THE INVENTION

The present inventors have recognized that, while the aforementioned methods for minimally invasive surgery are advantageous in many regards, they are also limited in certain aspects. In particular, the present inventors have recognized that there is a need for an improved method of presenting a physician with a display for use in surgical procedures that combines images from, for example, an endoscope, with three-dimensional images obtained via, for example, CT or MRI scanning. Therefore, the present inventors have invented a method and apparatus presenting such three-dimensional data to a physician for flexible navigation of an endoscope and surgical instruments with respect to anatomical structures. In accordance with a first embodiment, a first set of data corresponding to a three dimensional model of a patient's anatomy is received. This three-dimensional model may be rendered from images taken in CT or MRI scanning, as discussed above. In accordance with this embodiment, this model is then combined with a second set of data corresponding to a view obtained from an endoscope. In another embodiment, the view from the illustrative endoscope is displayed as an inset image on the display of the three-dimensional image. In yet another embodiment, the three-dimensional image comprises a graphical representation of at least a first surgical instrument, such as said endoscope. The surgeon may select among various combinations of views and may zoom in or out from any particular view.

These and other advantages of the invention will be apparent to those of ordinary skill in the art by reference to the following detailed description and the accompanying drawings.

DETAILED DESCRIPTION

Figure 1:
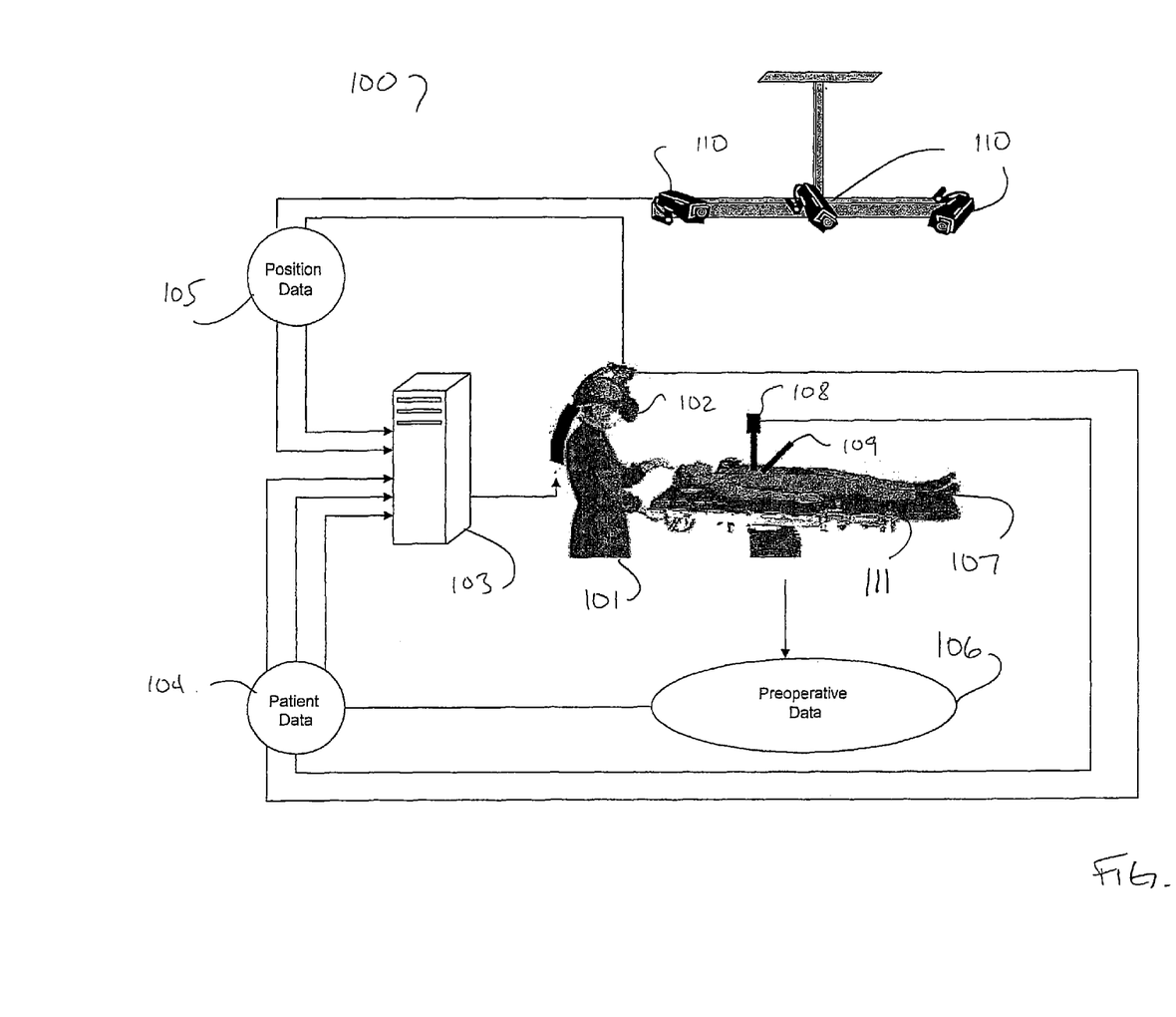
FIG. 1 shows an illustrative image visualization system in accordance with an embodiment of the present invention.

As discussed above, in order to perform difficult surgical tasks such as those difficult minimally-invasive tasks discussed above, it is desirable that a physician 101 has as much information as possible in regards to the positioning of the surgical instruments and endoscope with respect to anatomical structures. Therefore, in accordance with the principles of the present invention, a flexible navigation and visualization system is provided. FIG. 1 shows an illustrative endoscopic imaging, navigation and visualization system 100 in accordance with an embodiment of the present invention. Referring to that figure, physician 101 is illustratively a surgeon performing thoracoscopic surgery on patient 107 tying on surgical table 111. Surgeon 101 manipulates surgical instrument 109 to accomplish predetermined surgical tasks, such as removing material from between vertebrae in the spinal column of patient 107 or, alternatively, fusing multiple vertebrae together, as discussed above. Visualization system 100 also has, illustratively, computer 103, camera system 110 and endoscope 108 for producing images to assist physician 101 in performing surgery.

System 100 is capable of selectably presenting multiple views to physician 101. Specifically, at the physician's option, a variety of different views of the patient's anatomy and surgical site can be shown. These views can be a single type of view or, alternatively, a combination of views that best support the current surgical task. More particularly, the physician may select, illustratively, a global view, which is a virtual view from the perspective of the physician. In such a view, the current position and orientation of the surgical instruments and endoscope are tracked, as discussed further herein below, and are graphically shown in the context of a three-dimensional model of the patient's relevant anatomy. Such a global view may consist, for example, of a combination of preoperative images (e.g., CT or MRI scan images) of the patient, live visual images of the patient captured by one or more video cameras, and positional information of the medical instruments and the endoscope. This latter positional information may consist of graphical representations of the instruments and their movement with respect to the global view. In addition to the global view, in accordance with another embodiment of the invention, the physician can select for display a local view of the surgical site, which is an optical view from the perspective of the endoscope/thoracoscope. Such a view may also be enhanced with virtual images from the aforementioned preoperative CT or MRI scans.

In order to produce these views, various types of data must be collected and stored in illustrative computer 103 for use in system 100. As discussed above, this data can originate from a variety of sources. In particular, the aforementioned CT/MRI images can be obtained from preoperative CT/MRI scanning and the resulting image data stored in computer 103. This image data can be used, as discussed herein below, to create and display a virtual image of the patient, including internal anatomical features. In addition to this virtual data, one or more cameras in the operating room can provide live image data of the patient. Such cameras can be, illustratively, mounted on the ceiling of the operating room to provide, for example a stereoscopic live view of the patient. As also discussed above, images from the endoscope can also be collected and can then be stored in computer 103. Once this data is collected and available in computer 103, many different views may be created during surgery and displayed to the physician 101. Specifically, by linking and synchronizing the images and then combining some or all of the above data types together, as well as data related to the perspective of the surgeon and the location of the surgical instruments, a physician can select different views and different perspectives in order to guide the performance of surgical tasks and, in more particularity, the position of an endoscope or other surgical instrument while inside a patient's body.

Figure 2:
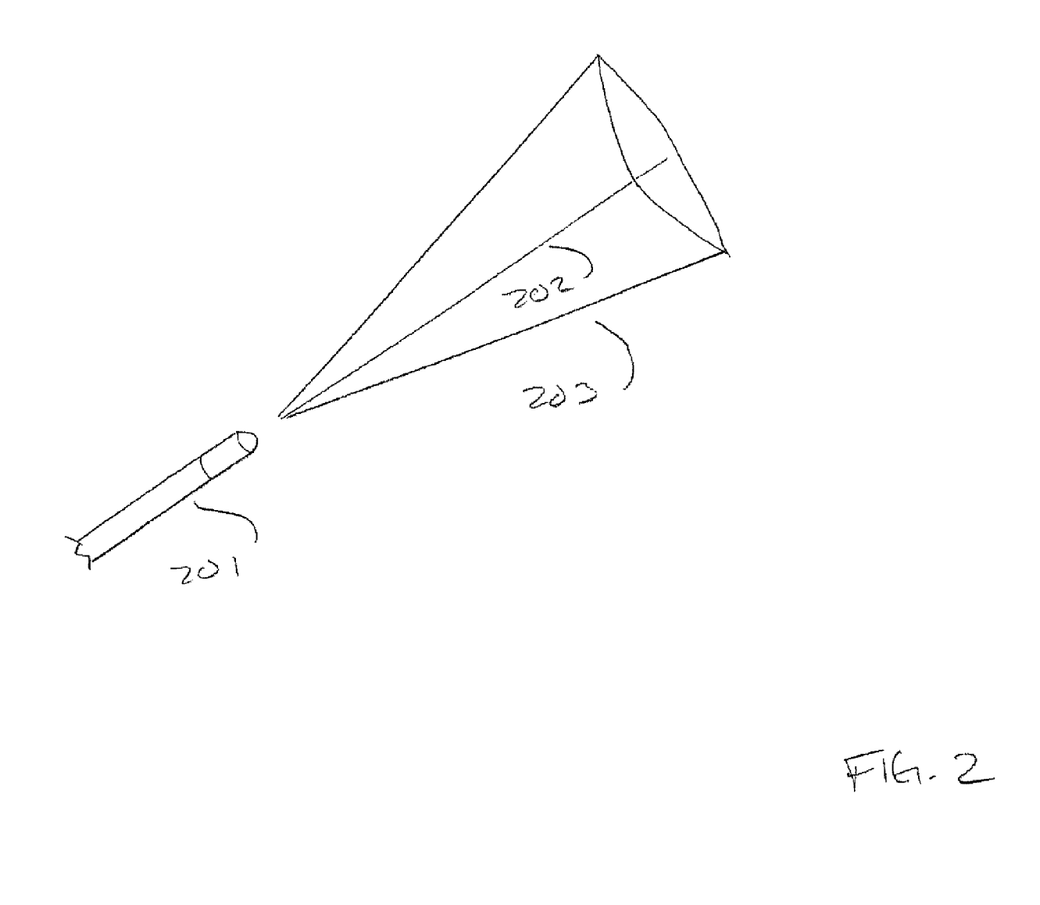
FIG. 2 shows an illustrative graphical representation of an endoscope.
Figure 3:
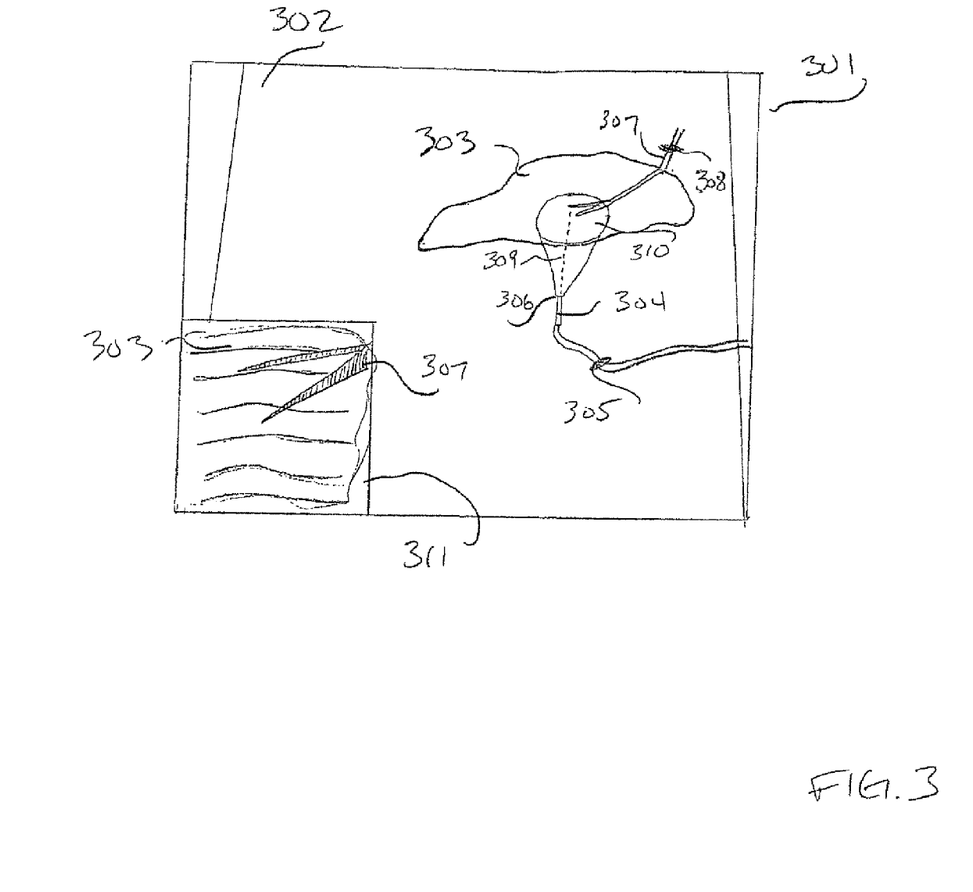
FIG. 3 shows an integrated display for visualization of images useful in surgical procedures.

In order to use the image data collected as discussed above, the images data must be linked and synchronized and, in addition, some method of providing perspective to a physician's view must be provided. Specifically, in accordance with other embodiments of the present invention, various different combinations of views are possible. First, in one embodiment, a virtual view of a patient is created for viewing by a surgeon. In order to create such a virtual view, as discussed above, preoperative CT or MRI virtual images are stored in the computer 103. By providing input as to the position and orientation of the surgeon and, more particularly, a surgeon's head and eyes, a view of the virtual images can be provided corresponding to that position and orientation. For example, such position and orientation information of a surgeon may be provided by a tracking device 102 in FIG. 1, such as an optical, magnetic, gimbaled or other well-known tracking device, worn by the surgeon on a head-mounted unit. By tracking the movements and orientation of the surgeon's head, and providing that information to the computer 103, the virtual images can be displayed in way such as to correspond to a global virtual view from the perspective of the surgeon. Once this virtual view is displayed, other display views may illustratively be combined in the display. For example, in accordance with another embodiment, a live optical endoscopic view can be inset into the virtual view, thus providing an actual view of the local surgical site near the endoscope. In yet another embodiment, the location of the endoscope, as well as illustratively the optical axis of the endoscope view (i.e., the viewing direction of the endoscope), can be graphically provided and displayed in the global virtual view. This view may also include a graphical cone corresponding to the field of view of the endoscope. Such a view is shown in FIG. 2. For example, referring to that figure, endoscope 201 is displayed in a graphical display having optical axis 202 and field of view cone 203, thus providing a surgeon with orientation information for the endoscope. This may then be combined with the global virtual view and the intersection of surface structures as imaged in the CT/MRI images. Thus, when coupled with the live optical view from the endoscope illustratively inset into the virtual view, the physician has both a global view of the patient, a graphical representation within that global view of the precise location and view of the endoscope, as well as a live optical local view of a patient's internal anatomy from the endoscope. In addition, in accordance with another embodiment, the live image from the endoscope can be mapped onto the surface structures rendered in the virtual scene. The resulting image would consist of a live image overlaid directly onto the virtual image in order to provide an integrated three-dimensional view of the local area of the endoscope. These images may, illustratively, be displayed in an augmented reality visualization in which a view captured by a video camera is combined with a virtual view, as described above. FIG. 3 shows how such an overlaid image might appear. Specifically, referring to that figure, display 301, which is illustratively a display of a stereographic headset on a surgeon's head, may show an image of a patient's body 302. This image is, illustratively, a live image of the outer surface of the patient's body as well as a virtual image of the internal anatomical structure comprising, for example, structure 303. As can be seen in this image, endoscope 304 is inserted through incision 305 to position 306. Medical instrument 307 is inserted through incision 308. Various tracking methods, discussed herein below, are used to present a graphical image of the endoscope 304 and instrument 307 for viewing on display 301. Display 301 also shows illustrative optical axis 309 of endoscope 304, as well as viewing angle cone 310. The intersection of viewing cone 310 is, also illustratively, mapped onto structure 303, providing feedback of the view endoscope 304 is capable of providing. A live view of endoscope 304 is shown in overlay window 311 and shows the surface of structure 303 as well as a portion of instrument 307. Thus, by monitoring both the graphical and live images displayed on display 301, a surgeon can obtain an overall detailed view of both the surgical procedure. A surgeon can then "zoom" from outside a patient's body to view a CT scan or MRI-based image of the internal anatomical structures at will. Such detailed and linked information greatly enhances the ability of the physician to perform difficult and delicate procedures.

In addition to providing the various live and virtual anatomical views described above, it is also necessary to have a precise view of the location and orientation of the surgical instruments, including the endoscope, for viewing in both integrated and stand-alone views. Such a precise view may be achieved by using a well-known tracking system, such as a marker-based optical tracking system or a magnetic tracking system. As one skilled in the art will recognize, such an optical tracking system may be used for tracking objects outside a patient's body while a magnetic system is useful for tracking the position of objects, such as medical instruments, while inside the patient's body. Optical tracking systems typically make use of passive (e.g., retro-reflective) or active (e.g., infrared) optical markers that are attached to the object to be tracked. The markers can be found relatively easily in infrared camera images. Then, via well-known image processing techniques, the two dimensional location and orientation of the markers in the image can be compared with the predetermined location of the markers on the object to be tracked. From this, the orientation of the instrument can be identified.

One skilled in the art will recognize, as discussed above, that such an optical tracking method is only useful for objects and markers that are external to a patient's body. Additionally, one skilled in the art will also recognize that such a method may be useful for rigid objects partially inserted into a patient's body. For example, when rigid endoscopes are used in medical procedures, the length and position of various portions of the endoscope that are inside a patient's body may be derived from the position of other portions of the device that are external to the patient's body. This is because the relative position of the different parts of the endoscope are known and do not change. Thus, for example, by placing optical markers on portions of the endoscope that are external to a patient's body, the position of the lens of the endoscope can be determined by comparing the relative three dimensional positions of the markers with the known location of those markers on the endoscope.

However, in order to track other devices, such as flexible endoscopes and medical devices that are substantially inserted into the patient's body, magnetic tracking systems may be preferable. Such magnetic tracking systems are also well known in the art. Similar to optical markers used in an optical tracking system, as discussed above, magnetic tracking systems typically rely on magnetic coils embedded into or attached to medical instruments. By generating a magnetic field and detecting the location of the sensor coils, the position and orientation of objects inside a patient's body can be determined.

Once the aforementioned image, perspective and instrument position and orientation data is collected, the above-described combined views can be selectably generated by a surgeon. One skilled in the art will recognize that careful registration and ongoing calibration of the various views as well as the positions and orientations of instruments is essential to maintaining the accuracy of the integrated views described herein above. Specifically, if the imaging system is well calibrated and the image models are correctly registered to their real counterparts (e.g., anatomic models correspond closely to the real anatomy of the patient and instrument models are correctly registered to the real instruments), the global virtual view will show the position of the instruments (i.e., instrument tips) in correct spatial arrangement to those anatomical structures. Such methods of calibration and registration involve various methods of three-dimensional texture mapping and image recognition and are well known in the art. Thus, such methods will not be described in detail herein. However, once such registration and calibration has occurred, it can be quickly verified by the physician by bringing an instrument into contact with an anatomical surface. If the virtual views and representations of the instrument match the optical view of the instruments (i.e., the sensors indicate that an instrument contacts a surface when the optical view shows such contact occurring), then the calibration and registration have been accomplished correctly.

In the event of an apparent registration error, the user may in accordance with another embodiment, choose to update the registration. Specifically, with a tracked instrument, for example, the user can collect coordinates of anatomical landmarks and/or of surface points of anatomical structures such as bones. Using algorithms well known in the art, these points can be registered (i.e., compared and matched to) the three-dimensional medical live or virtual medical images described above. For example, relevant anatomical structures may be identified in a three-dimensional medical image and the acquired points of actual anatomical structures can be registered to the medical images using a well-known iterative closest point algorithm.

Once correct registration has been achieved, a user can monitor the progress of surgical procedures and update virtual anatomical models (e.g., those generated from CT and/or MRI scans), in a similar fashion. Specifically, a user will collect coordinates of internal anatomical structures and will then register them with into these virtual models. Once this registration has occurred, if, for example, an anatomical structure is removed from the patient, the virtual model can be updated to reflect this removed structure by contacting various points along the remaining anatomical structures and recording the points of contact.

One skilled in the art will recognize that various functionalities can be added to the above-described visualization system. First, various methods of zooming into or away from various points on the views is possible. Such a zooming function provides a surgeon with any desired viewing distance from a surgical site in order to provide a desired perspective. In addition, other various methods of displaying various views are possible. For example, a head-mounted display may provide a stereoscopic view that includes both virtual images as well as live images. Alternatively, any of these images may be displayed on an external display. These images may be recorded, for example, by computer 103 in FIG. 1 for later viewing. Other variations on viewing the various displays of the information discussed herein will be obvious to one skilled in the art in light of the foregoing discussion.

Figure 4:
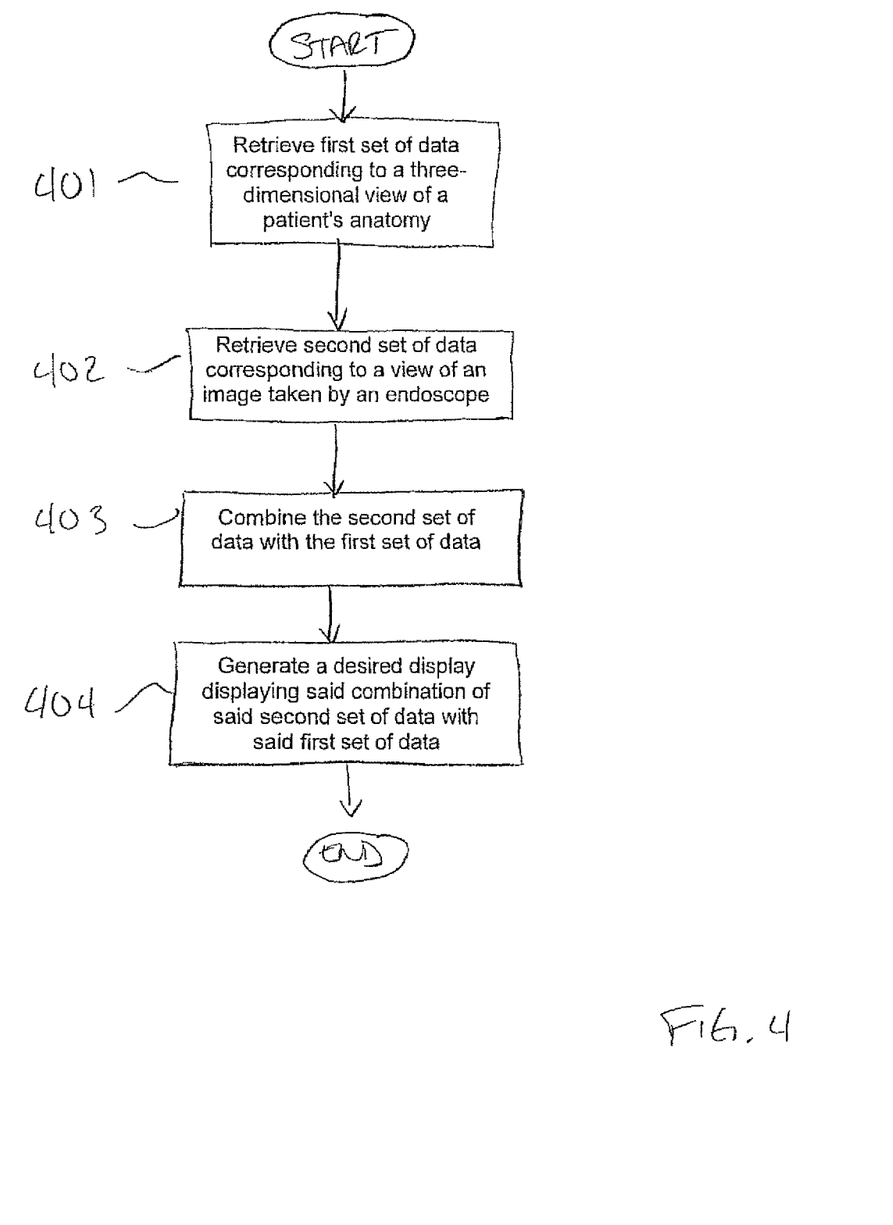
FIG. 4 shows a method in accordance with an embodiment of the present invention.

FIG. 4 shows a method for use in providing a display for a surgical procedure in accordance with the principles of the invention described herein above. Referring to that figure, at step 401, a first set of data corresponding to a three-dimensional view of a patient's anatomy is retrieved. At step 402, a second set of data corresponding to a view of an image taken by an endoscope is retrieved. Then, at step 403, the second set of data is combined with the first set of data to produce a desired display to, for example, a surgeon.

Figure 5:
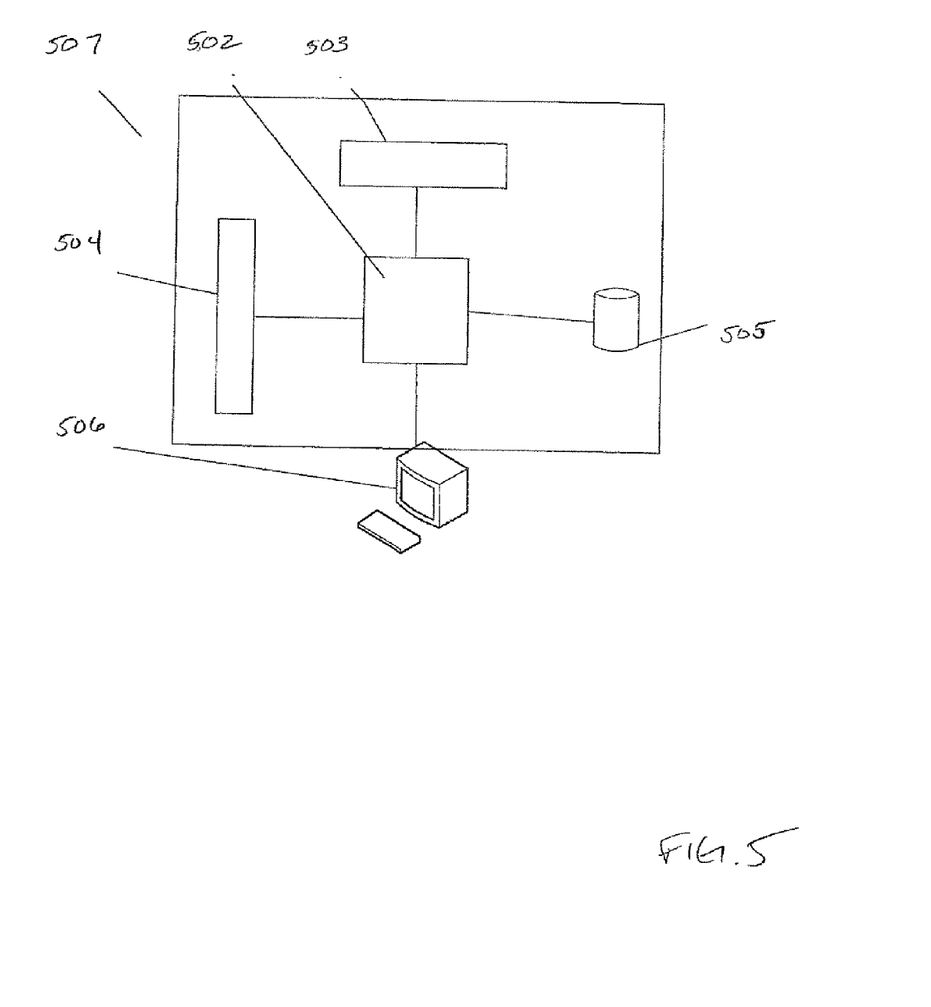
FIG. 5 shows a schematic diagram of a computer adapted to perform the steps of a computer program to calculate and display visualization data in a three-dimensional visualization system in accordance with an embodiment of the present invention.

One skilled in the art will recognize that a three-dimensional visualization system, such as that described above, may be implemented on a programmable computer adapted to perform the steps of a computer program to calculate the positional and visualization data as described herein. Referring to FIG. 5, such a visualization system 507 may be implemented on any suitable computer adapted to receive, store and transmit data such as the aforementioned patient and positional information. Specifically, illustrative visualization system 507 may have, for example, a processor 502 (or multiple processors) which controls the overall operation of the visualization system 507. Such operation is defined by computer program instructions stored in a memory 503 and executed by processor 502. The memory 503 may be any type of computer readable medium, including without limitation electronic, magnetic, or optical media. Further, while one memory unit 503 is shown in FIG. 5, it is to be understood that memory unit 503 could comprise multiple memory units, with such memory units comprising any type of memory. Visualization system 507 also comprises illustrative modem 501 and network interface 504. Visualization system 507 also illustratively comprises a storage medium, such as a computer hard disk drive 505 for storing, for example, data and computer programs adapted for use in accordance with the principles of the present invention as described hereinabove. Finally, visualization system 507 also illustratively comprises one or more input/output devices, represented in FIG. 5 as terminal 506, for allowing interaction with, for example, a technician or database administrator. One skilled in the art will recognize that visualization system 507 is merely illustrative in nature and that various hardware and software components may be adapted for equally advantageous use in a computer in accordance with the principles of the present invention.

One skilled in the art will also recognize that the software stored in computer system of FIG. 5 may be adapted to perform various tasks in accordance with the principles of the present invention. In particular, such software may be graphical software adapted to import surface models from anatomical structures, for example those models generated from three-dimensional medical images such as CT or MRI images. In addition, such software may allow for selective visualization in a way that allows a user to select which anatomical structures to include in a virtual view as described above. The computer system may be adapted to receive real time tracking information and to display models of the instruments in virtual views of the anatomical models. Such software may also permit the reception and display of real time endoscopic images as well as the switching between real time images and virtual views. Alternatively, such software may be adapted to combine real time views with virtual views of anatomical structures. The software of a computer-based system such as visualization system 507 may also be adapted to perform other functions which will be obvious in light of the teachings herein. All such functions are intended to be contemplated by these teachings.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method of providing a display for use in a surgical procedure comprising:
    receiving a first set of data corresponding to a view of an image taken by an endoscope;
    combining said first set of data with a second set of data to produce a three-dimensional combined image, said second set of data corresponding to a three-dimensional model of an anatomical structure of a patient, said three-dimensional combined image comprising the image taken by the endoscope mapped onto a surface of the three-dimensional model of the anatomical structure of the patient to provide an integrated three-dimensional view of a local area of the endoscope;
    receiving a third set of data corresponding to positional data of a surgical instrument; and
    combining said third set of data with said second set of data to produce a graphical representation of said surgical instrument on said display,
    wherein said third set of data comprises data representing an optical field of view of said endoscope, said combined image comprises a display of the intersection of said optical field of view with the 3D model of the anatomical structure in the patient's body, and said combined image comprises an image created by texture mapping said optical field of view of said endoscope onto the surface of the three-dimensional model of the anatomical structure of the patient.

2. The method of claim 1 wherein said combined image comprises a global view from the perspective of a user performing said surgical procedure.

3. The method of claim 1 wherein said combined image comprises a local view from the perspective of said endoscope.

4. The method of claim 1 wherein said second set of data comprises data corresponding to an image collected by a computed tomography or magnetic resonance imaging process.

5. The method of claim 4 wherein said combined image comprises a stereoscopic augmented reality visualization.

6. The method of claim 4 wherein said step of combining comprises displaying said first set of data as a first view inset as a video image in a second view, said second view providing a view of a portion of said image collected by a computer tomography or magnetic resonance imaging process.

7. The method of claim 6 wherein said first view comprises a two dimensional image inset into said second view.

8. The method of claim 1 further comprising:
receiving an input from a user; and
displaying an image associated with said first set of data or said second set of data in response to receiving said input.

9. The method of claim 1 wherein said combined image comprises an image from the perspective of said surgical instrument.

10. The method of claim 1 wherein said third set of data comprises data representing the optical axis of said endoscope.

11. The method of claim 1 wherein said third set of data comprises data representing the orientation of said surgical instrument.

12. The method of claim 1 wherein said positional data is data obtained by a tracking system.

13. The method of claim 12 wherein said tracking system comprises an infrared optical tracking system adapted to determine the position of at least a first optical marker.

14. The method of claim 12 wherein said tracking system comprises a magnetic tracking system adapted to determine the position of at least a first magnetic coil.

15. The method of claim 1 wherein said surgical instrument comprises a tracked pointer.

16. The method of claim 15 further comprising:
determining at least a first position of said tracked pointer in order to register an anatomical model of said patient to said patient's anatomy.

17. The method of claim 15 further comprising:
determining at least a first position of said tracked pointer in order to update an anatomical model of said patient during said surgical procedure.

18. An apparatus for providing a display for use in a surgical procedure comprising:
means for receiving a first set of data corresponding to a view of an image taken by an endoscope;
means for combining said first set of data with a second set of data to produce a three-dimensional combined image, said second set of data corresponding to a three-dimensional model of an anatomical structure of a patient, said three-dimensional combined image comprising the image taken by the endoscope mapped onto a surface of the three-dimensional model of the anatomical structure of the patient to provide an integrated three-dimensional view of a local area of the endoscope;
means for receiving a third set of data corresponding to positional data of a surgical instrument;
means for combining said third set of data with said second set of data to produce a graphical representation of said surgical instrument; and
means for displaying said graphical representation of said surgical instrument,
wherein said third set of data comprises data representing an optical field of view of said endoscope, said combined image comprises a display of the intersection of said optical field of view with the 3D model of the anatomical structure in the patient's body, and said combined image comprises an image created by texture mapping said optical field of view of said endoscope onto the surface of the three-dimensional model of the anatomical structure of the patient.

19. The apparatus of claim 18 wherein said combined image comprises a global view from the perspective of a user performing said surgical procedure.

20. The apparatus of claim 18 wherein said combined image comprises a local view from the perspective of said endoscope.

21. The apparatus of claim 18 wherein said second set of data comprises data corresponding to an image collected by a computed tomography or magnetic resonance imaging process.

22. The apparatus of claim 18 further comprising:
means for varying the magnification of at least a portion of said combined image.

23. The apparatus of claim 21 wherein said combined image comprises a stereoscopic augmented reality visualization.

24. The apparatus of claim 21 wherein said means for combining comprises means for displaying said first set of data as a first view inset as a video image in a second view, said second view comprising a view of a portion of said image collected by a computer tomography or magnetic resonance imaging process.

25. The apparatus of claim 18 wherein said combined image comprises an image from the perspective of said surgical instrument.

26. The apparatus of claim 18 wherein said third set of data comprises data representing the optical axis of said endoscope.

27. The apparatus of claim 18 wherein said third set of data comprises data representing the orientation of said surgical instrument.

28. The apparatus of claim 18 wherein said positional data is data obtained from a tracking system.

29. The apparatus of claim 28 wherein said tracking system comprises an infrared optical tracking system adapted to determine the position of at least a first optical marker.

30. The apparatus of claim 28 wherein said tracking system comprises a magnetic tracking system adapted to determine the position of at least a first magnetic coil.

31. The apparatus of claim 18 wherein said surgical instrument comprises a tracked pointer.

32. The apparatus of claim 31 further comprising:
determining at least a first position of said tracked pointer in order to register an anatomical model of said patient to said patient's anatomy.

33. A non-transitory computer readable medium comprising computer program instructions which, when executed by a processor, define steps for providing a display for use in a surgical procedure, said steps comprising:
receiving a first set of data corresponding to a view of an image taken by an endoscope;
combining said first set of data with a second set of data to produce a three-dimensional combined image, said second set of data corresponding to a three-dimensional model of an anatomical structure of a patient, said three-dimensional combined image comprising the image taken by the endoscope mapped onto a surface of the three-dimensional model of the anatomical structure of the patient to provide an integrated three-dimensional view of a local view of the endoscope;
receiving a third set of data corresponding to positional data of a surgical instrument; and combining said third set of data with said second set of data to produce a graphical representation of said surgical instrument, wherein said combined image comprises an image of the intersection of an optical field of view of said endoscope with the 3D model of the anatomical structure in the patient's body and said combined image comprises an image created by texture mapping said optical field of view of said endoscope onto the surface of the three-dimensional model of the anatomical structure of the patient.

34. The computer readable medium of claim 33 wherein said combined image comprises a global view from the perspective of a user performing said surgical procedure.

35. The computer readable medium of claim 33 wherein said combined image comprises a local view from the perspective of said endoscope.

36. The computer readable medium of claim 33 wherein said second set of data comprises data corresponding to an image collected by a computed tomography or magnetic resonance imaging process.

37. The computer readable medium of claim 36 wherein said computer program instructions which, when executed by a processor, define said step of combining comprise computer program instructions which, when executed by a processor, define the step of displaying said first set of data as a first view inset as a video image in a second view, said second view providing a view of a portion of said image collected by a computer tomography or magnetic resonance imaging process.

38. The computer readable medium of claim 33 wherein said combined image comprises an image from the perspective of said surgical instrument.

39. The computer readable medium of claim 33 wherein said positional data is obtained by a tracking system, said tracking system comprising an infrared optical tracking system adapted to determine the position of at least a first optical marker.

40. The computer readable medium of claim 33 wherein said surgical instrument comprises a tracked pointer.

41. The computer readable medium of claim 40 further comprising computer program instructions which, when executed by a processor, define the step of:

determining at least a first position of said tracked pointer in order to register an anatomical model of said patient to said patient's anatomy.

* * * * *